United States Patent [19]

Yung-Ho

[11] Patent Number: 4,718,892
[45] Date of Patent: Jan. 12, 1988

[54] DRIP INFUSION SYSTEM

[76] Inventor: Liu Yung-Ho, 14th Room, 13th Fl., No. 4, Hsi-ning S. Road, Taipei City, Taiwan

[21] Appl. No.: 837,205

[22] Filed: Mar. 10, 1986

[51] Int. Cl.$^4$ .............................................. A61M 5/16
[52] U.S. Cl. ........................................ 604/65; 604/81
[58] Field of Search ................ 604/65, 67, 66, 244, 604/81

[56] References Cited

U.S. PATENT DOCUMENTS

| 3,578,774 | 5/1971 | McDonald | 604/67 |
| 4,137,915 | 2/1979 | Kamen | 604/65 |
| 4,447,226 | 5/1984 | Mayoral | 604/32 |
| 4,457,750 | 7/1984 | Hill | 604/65 |
| 4,475,668 | 10/1984 | Kawakami et al. | 604/65 |

Primary Examiner—Stephen C. Pellegrino
Assistant Examiner—Ralph Lewis
Attorney, Agent, or Firm—Angelo Notaro

[57] ABSTRACT

A drip infusion system is disclosed in which a pulling mechanism is connected to a needle for automatically pulling the needle from the vein of a patient. The pulling mechanism is actuated to pull the needle from the vein responsive to the amount of solution in a drip source mounted on a stand.

7 Claims, 5 Drawing Figures

DRIP INFUSION SYSTEM

BACKGROUND OF THE INVENTION

The present invention relates to a drip infusion system, and more particularly to a drip infusion system which pulls the injecting needle from the vein of a patient automatically when the drip is finished. The system also permits a plurality of drip bottles to be used simultaneously.

Drip infusion is prevalently used in the hospital for the slow continued administration of a fluid, such as liquid glucose or isotonic sodium chloride solution, contained in a drip bottle at a steady rate especially into a vein of a patient via a tube and an injecting needle. In use, the conventional drip bottle is suspended on a drip infusion stand or the like at a high position, and the solution of drug or nutrient in the drip bottle is injected into the vein by needle via a tube connected between the drip bottle and the needle due to gravity. This conventional drip device has two disadvantages.

Since most patients need to be infused from several bottles continuously, the nurse must pay constant attention to notice whether the solution in one bottle is exhausted in order to change to the new bottle to continue the infusion in time.

In some cases, the needle is not pulled out in time after the solution is exhausted, resulting in blood flow up into the tube through the needle.

An improved drip infusion system in accordance with one preferred embodiment of the present invention intends to improve on the disadvantages described above.

SUMMARY OF THE INVENTION

The primary object of the present invention is to provide a drip infusion system which can pull the needle automatically from the vein of the patient when the infusion is finished.

Another object of the present invention is to provide an improved drip infusion system with a plurality of drip bottles which permits the drip operation to proceed simultaneously without changing the bottles one by one.

Yet another object of the present invention is to provide an improved drip infusion system which utilizes a pulling means acutated by electrical power to achieve the automatic pulling process for the needle.

Yet another object of the present invention is to provide an improved drip infusion system which utilizes a shut-off means to shut off the electrical power connected to the pulling means after the needle is pulled from the vein of a patient.

In accordance with one preferred embodiment of the present invention, an improved drip infusion system comprises a drip device adapted for being movably secured to a drip infusion stand; a needle device connected to the drip device for injecting the solution contained in the drip device into a vein of a patient; and means for pulling the needle device from the vein of the patient automatically. The pulling means being actuated by the drip device when the solution in the drip device is below a predetermined amount.

In accordance with another aspect of the present invention, the drip device includes a spring secured to the drip infusion stand at one end, at least two drip bottles, the first drip bottle being secured to the drip infusion stand and the second drip bottle being suspended by the spring at a position below the first drip bottle, and a collecting box connected to the drip bottles and to the needle device to collect the solutions from the drip bottles to send to the needle device. The pulling means includes a first microswitch arranged above the second drip bottle, so that when the second drip bottle is moved upwards by the spring due to the fact that the solution therein is reduced to the predetermined amount, the top of the second bottle will press the first microswitch to activate the pulling means.

In accordance with yet another aspect of the present invention, the drip infusion system further comprises means for shutting off the power source connected to the pulling means. The shutting off means includes a second microswitch mounted in a position to be switched on by the pulling means after the needle is pulled out, and a relay coupled to the second microswitch and the power source respectively for being switched on by the switch-on of the second microswitch to turn off the power source.

BRIEF DESCRIPTION OF THE DRAWINGS

The present invention will be more fully understood from the following detailed description, taken in connection with the accompanying drawings which form an internal part of this application and in which.

DETAILED DESCRIPTION OF THE PREFERRED EMBODIMENT

Figure 1:
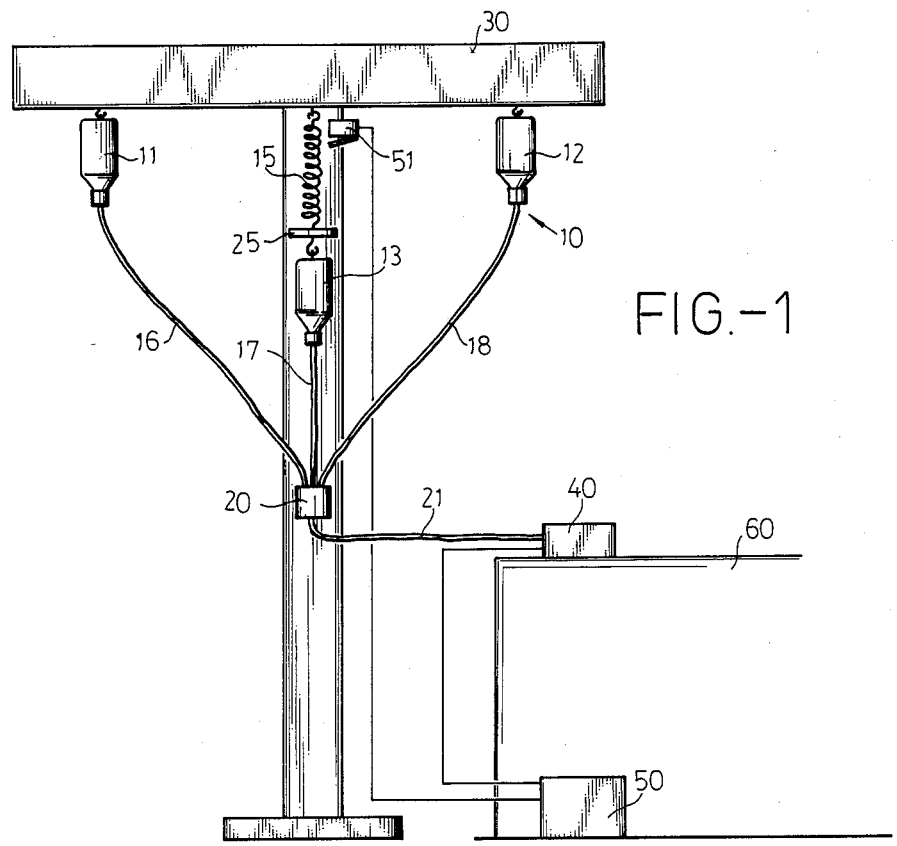
FIG. 1 is a schematic view of the drip infusion system in accordance with one preferred embodiment of the present invention.

Referring now to the drawings, it should be noted that a like member is designated with a like reference number. With reference to FIG. 1, there is shown a drip infusion system in accordance with one preferred embodiment of the present invention. The drip infusion system includes a drip device 10, a needle device 40 connected to the drip device 10, and means 50 for pulling the needle device 40 from a vein of a patient automatically. The needle device 40 is utilized to inject the solution contained in the drip device 10 into the vein of the patient laying on bed 60.

The drip device 10 includes a spring 15 secured to a drip infusion stand 30 or the like at one end, three drip bottles 11 to 13, two 11 and 12 being secured to the drip infusion stand 30, one 13 being suspended by spring 15, and a collecting box 20 connected to the drip bottles 11, 12 and 13 through three tubes 16, 17 and 18 to the needle device 40 through a tube 21. The collecting box 20 collects the solutions, such as liquid glucose or isotonic sodium chloride solution, from the drip bottles 11, 12 and 13 and sends the solution to the needle device 40. The drip bottle 13 is arranged in a position below the other drip bottles 11 and 12 so that the solutions contained in the drip bottles 11 and 12 are exhausted before the solution in drip bottle 13 due to the U-shaped tube's principle. As the solution in the drip bottle 13 reduces gradually, the drip bottle 13 moves upward by the biasing force of spring 15. The lower end of the spring 15 may be provided with actuating plate 25.

Figure 3:
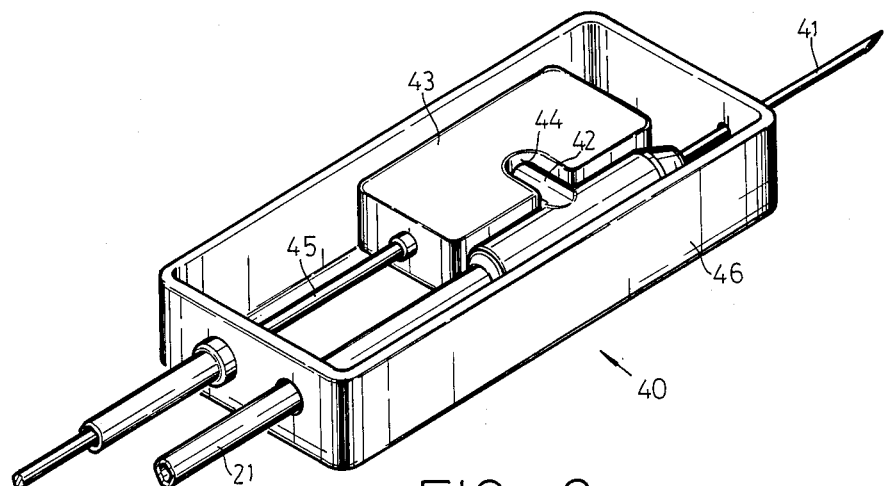
FIG. 3 is a perspective view of the needle device of the present invention.

Refering to FIGS. 1 and 3, the needle device 40 includes a needle 41 connected to the collecting box 20 through the tube 21 having an engaging portion 42 at its rear, a sliding block 43 having a recess 44 to engage with engaging portion 42 of needle 41 connected to the pulling means 50 through a line 45, and an accommodating casing 46 used to accommodate the sliding block 43 and the needle 41 therein. The accommodating casing 46 has three holes to allow the passages of line 45, tube 21 and needle 41.

Figure 2:
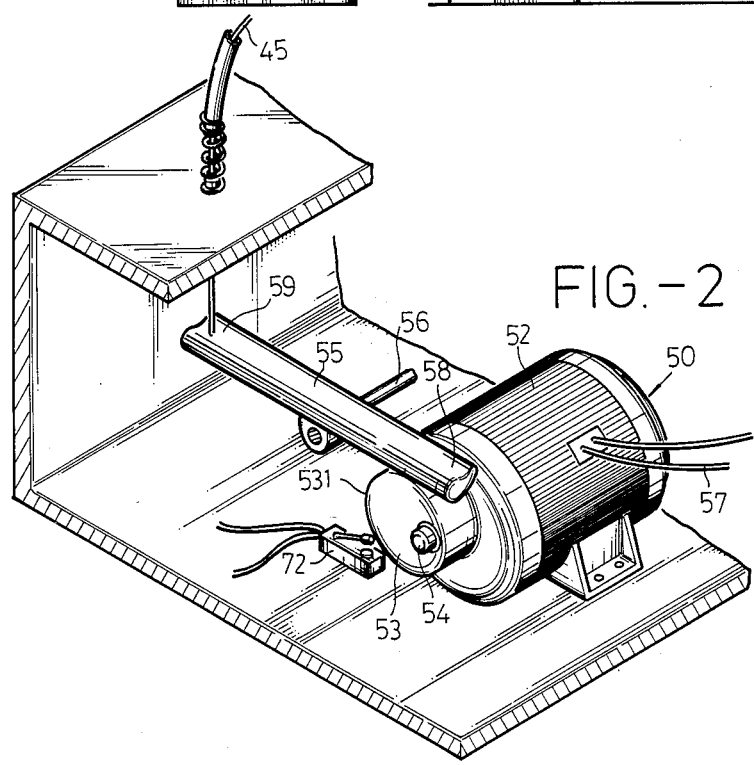
FIG. 2 is a perspective view of the pulling means of the present invention.

With reference to FIGS. 1 to 3, the pulling means 50 includes a first microswitch 51 arranged above the drip bottle 13, a motor 52, a cam 53 fixed about the rotating shaft 54 of the motor 52 eccentrically, and a lever 55 fastened rotatably at point 56. The motor 52 is coupled to the power source via the first microswitch 51 by the lines 57. End 58 of the lever 55 is positioned on the circumferential surface of the cam 53, and the other end 59 of the lever 55 is connected to the line 45. As the drip bottles 11 and 12 empty and the solution in the drip bottle 13 falls below a predetermined amount, drip bottle 13 moves upward to an extent by spring 15, so that actuating plate 25 above the drip bottle 13 will press the first microswitch 51 to switch on motor 52. When the motor 52 is coupled to a power source, the cam 53 will be rotated by rotating shaft 54. Since the cam 53 is mounted on rotating shaft 54 eccentrically, its part 531 is at a further distance from the rotating shaft 54 and will push the end 58 of lever 55 to a uppermost position while the other end 59 is moved to a lowermost position. In this case, line 45 is pulled downward to draw sliding block 43 with needle 41 rearward away from the vein of the patient. Therefore, the drip process is finished automatically without any care from a nurse. The accommodating casing 46 is utilized to ensure steady movements of the needle and the sliding block, and prevents the needle 41 from pricking the patient further when the needle 41 is fully drawn into the accommodating casing.

It should be understood that the drip bottle of drip device 10 is not limited to three as shown in FIG. 1, two or more drip bottles may be used to achieve the same function as described above.

Figure 4:
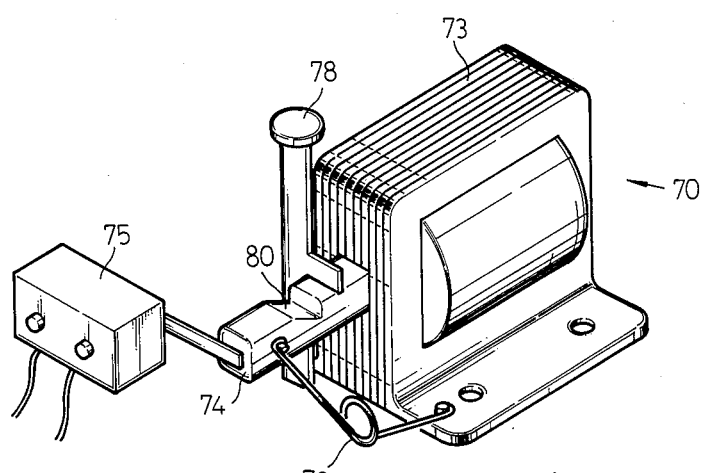
FIG. 4 is a perspective view of the shutting off means of the present invention.
Figure 5:
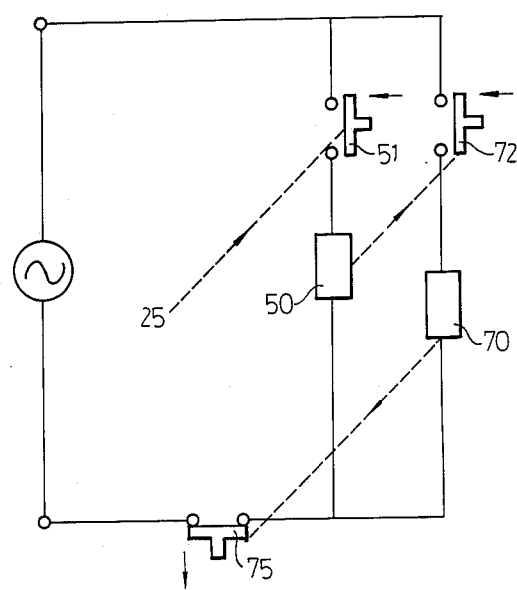
FIG. 5 is an electronic circuit diagram of the present invention.

Since the power source is not needed further after the needle is pulled away from the vein of the patient, the drip infusion system is preferably provided means 70 for shutting off the power source coupled to the motor 52 after the drip is finished automatically. With reference to FIGS. 2 and 4, the shutting off means 70 includes a second microswitch 72 mounted under cam 53 and a relay 73 coupled to second microswitch 72. When relay 73 is off, its core 74 abuts against a third microswitch 75 coupled to the power source. In this case, the third microswitch 75 is switched on, and the electrical power will be sent to motor 52 through relay 73. For ensuring the firm connection between the core 74 and the third microswitch 75, a spring 76 is preferably engaged to urge core 74 to contact the third microswitch 75 steadily and firmly.

After cam 53 pushes lever 55 to its uppermost position, part 531 of the cam 53 is rotated downward continuously to its lowermost position to press second microswitch 72. When the second microswitch 72 is switched on, the relay 73 is on and its core 74 is departed from the third microswitch 75. Therefore, the electrical power coupled to the motor 52 is shut off automatically. For ensuring the core 74 in a position without contacting the third microswitch 75 even when the power source is shut off, a lock element 78 may be provided to engage with a notch 80 on the core 74 when the core 74 is moved rearwards to relay 73.

While the invention has been described in connection with what is presently considered to be the most practical and preferred embodiment, it is to be understood that the invention is not so limited and covers various modifications and equivalent arrangements included within the spirit and scope of the appended claims which scope is to be accorded the broadest interpretation so as to encompass all such modifications and equivalent structures.

What I now claim is:

1. In a drip infusion system for the drip infusion of a solution into a vein of a patient, the system being of the type having a stand, a drip source containing the solution mounted on the stand, a needle removably inserted into the patient, and a conduit connected to the drip source and the needle for passing solution from the drip source to the needle and into the vein of the patient, the improvement comprising, in combination therewith, pulling means operatively connected to the needle for automatically pulling the needle out of the vein, and actuating means for actuating said pulling means to pull the needle out of the vein responsive to the amount of solution in the drip source.

2. In a drip infusion system as set forth in claim 1, the improvement wherein said drip source comprises at least a first drip bottle and a second drip bottle, the first drip bottle being fixedly secured to the stand, collecting means interconnected with the conduit for collecting solution from each of the first and second drip bottles and passing the collected fluid to the patient, pulling means operatively connected to the needle for removably pulling the needle out of the vein, first switch means mounted to the stand above the second bottle at a position below the first bottle for urging the second drip bottle upwardly into contact with the first switch means when the solution in the second drip bottle is reduced to a predetermined amount thereby causing the first switch means to activate the pulling means whereby the pulling means removes the needle from the vein.

3. In a drip infusion system as set forth in claim 2, the improvement wherein the pulling means comprises a motor, operatively connected to the first switch means, having a rotatable shaft and a cam fixed to the rotatable shaft, the cam having a peripheral surface for eccentric movement responsive to the rotation of the shaft, a lever pivotally mounted proximate to the cam having a first end on the peripheral surface and a second end, a line connected at its one end to said second end of the lever and the other end of the line being operatively connected to the needle, said motor being operable responsive to actuation by said first switch means to rotate the cam, wherein the first end of the lever moves in first direction responsive to the rotation of the cam and the said second end of the lever moves in a second directon opposite the first direction thereby pulling the line for pulling the needle from the vein.

4. In a drip infusion system as set forth in claim 3, wherein the needle includes an engaging portion, a slidable block interconnected to the engaging portion and the said other end of the line.

5. In a drip infusion system as set forth in claim 4, the improvement further comprising a casing housing said sliding block and the engaging portion of the needle, the casing having an aperture through which a portion of the needle extends for engaging the vein, said sliding block being slidable within the casing responsive to pulling of the line and moveable to a position within the casing in which the needle is fully contained within the casing thereby preventing the needle from pricking the patient.

6. In a drip infusion system as set forth in claim 5, the improvement further comprising a power source connected to said motor, means for shutting off the power source including second switch means mounted under the cam in a position to be actuated after said cam is rotated, and a relay electrically connected to the second switch means and the power source, the relay being operable responsive to the actuation of the second switch means to shut off the power source.

7. In a drip infusion system as set forth in claim 5, the improvement wherein each of the first and second switch means comprises a micro switch.

* * * * *